(12) United States Patent
Kim et al.

(10) Patent No.: US 10,884,504 B2
(45) Date of Patent: Jan. 5, 2021

(54) WEARABLE WRIST DEVICE AND METHOD OF DETECTING A PHYSICAL CHANGE IN THE EPIDERMIS AND WIRELESSLY INPUTTING SENSOR INFORMATION USING THE SAME

(71) Applicant: KOREA ELECTRONICS TECHNOLOGY INSTITUTE, Seongnam-si (KR)

(72) Inventors: Kunnyun Kim, Yongin-si (KR); Kwang Bum Park, Yongin-si (KR); Won Hyo Kim, Yongin-si (KR); Yeon Hwa Kwak, Seoul (KR)

(73) Assignee: KOREA ELECTRONICS TECHNOLOGY INSTITUTE, Seongnam-si (KR)

(*) Notice: Subject to any disclaimer, the term of this patent is extended or adjusted under 35 U.S.C. 154(b) by 68 days.

(21) Appl. No.: 15/873,786

(22) Filed: Jan. 17, 2018

(65) Prior Publication Data
US 2018/0143697 A1 May 24, 2018

Related U.S. Application Data

(63) Continuation of application No. PCT/KR2015/007468, filed on Jul. 17, 2015.

(51) Int. Cl.
*G06F 3/01* (2006.01)
*A61B 5/103* (2006.01)
(Continued)

(52) U.S. Cl.
CPC .............. *G06F 3/017* (2013.01); *G06F 3/011* (2013.01); *G06F 3/014* (2013.01); *A61B 5/103* (2013.01);
(Continued)

(58) Field of Classification Search
CPC ....................................................... G06F 3/017
See application file for complete search history.

(56) References Cited

U.S. PATENT DOCUMENTS 5,818,359 A * 10/1998 Beach ..................... G06F 3/011
341/21
6,244,873 B1 * 6/2001 Hill ......................... G06F 3/015
379/110.01
(Continued)

FOREIGN PATENT DOCUMENTS

KR 10-0634494 B1 10/2006
KR 10-2010-0074461 A 7/2010
(Continued)

OTHER PUBLICATIONS

Hwang, "Sensor-based Recognition of Human's Hand Motion for Control of a Robotic Hand", Journal of the Korea Academia-Industrialcooperation Society, 2014, vol. 15, No. 9, pp. 5440-5445.
(Continued)

*Primary Examiner* — Tammara R Peyton
(74) *Attorney, Agent, or Firm* — Knobbe Martens Olson & Bear LLP

(57) ABSTRACT

A wearable device is disclosed. In one embodiment, the device includes: a sensor array having a plurality of sensors each detecting a physical change in epidermis of a corresponding body area and a body movement determination unit configured to determine movement of a body part based on sensing signals respectively received from the plurality of sensors.

8 Claims, 8 Drawing Sheets

(51) Int. Cl.
 *A61B 5/00* (2006.01)
 *G06F 3/0346* (2013.01)
(52) U.S. Cl.
 CPC ............ *A61B 5/681* (2013.01); *G06F 3/0346* (2013.01); *G06F 2203/0384* (2013.01)

(56) References Cited

U.S. PATENT DOCUMENTS

| | | | | |
|---|---|---|---|---|
| 6,640,202 | B1* | 10/2003 | Dietz | A41H 1/02 342/118 |
| 7,101,287 | B1* | 9/2006 | Wagner | A63B 69/3608 473/207 |
| 8,292,833 | B2* | 10/2012 | Son | A61B 5/1126 250/316.1 |
| 8,704,757 | B2* | 4/2014 | Kurashima | G06F 3/014 15/72 |
| 9,971,313 | B2* | 5/2018 | Chung | G06F 1/163 |
| 10,137,362 | B2* | 11/2018 | Buchanan, IV | A63F 13/42 |
| 10,191,574 | B2* | 1/2019 | Shin | H04M 1/0268 |
| 10,488,937 | B2* | 11/2019 | Krasnow | A61B 8/58 |
| 2014/0028546 | A1* | 1/2014 | Jeon | G06F 3/014 345/156 |
| 2016/0299570 | A1* | 10/2016 | Davydov | G06F 1/163 |
| 2018/0160940 | A1* | 6/2018 | Kim | G06F 3/016 |

FOREIGN PATENT DOCUMENTS

| | | |
|---|---|---|
| KR | 10-2011-0022520 A | 3/2011 |
| KR | 10-1130150 B1 | 3/2012 |
| KR | 10-2014-0013845 A | 2/2014 |
| KR | 10-1413539 B1 | 7/2014 |
| KR | 10-2015-0112741 A | 10/2015 |
| WO | WO-2011055326 A1 * 5/2011 ............ G06F 3/015 |

OTHER PUBLICATIONS

International Search Report dated May 26, 2016 of PCT/KR2015/007468 which is the parent application—2 pages.

* cited by examiner

BEFORE GRABBING MOVEMENT

AFTER GRABBING MOVEMENT

BEFORE TWISTING WRIST

AFTER TWISTING WRIST

BEFORE STRETCHING FINGER

AFTER STRETCHING FINGER

BEFORE MOVING WRIST DOWNWARD
—WHEN WRIST IS SNAPPED

AFTER MOVING WRIST DOWNWARD

WEARABLE WRIST DEVICE AND METHOD OF DETECTING A PHYSICAL CHANGE IN THE EPIDERMIS AND WIRELESSLY INPUTTING SENSOR INFORMATION USING THE SAME

CROSS-REFERENCE TO RELATED APPLICATIONS

This application is a continuation application, and claims the benefit under 35 U.S.C. §§ 120 and 365 of PCT Application No. PCT/KR2015/007468, filed on Jul. 17, 2015, which is hereby incorporated by reference.

BACKGROUND

Field

The present disclosure relates to a wearable device and a method of inputting information using the same, and more specifically to an input device, which recognizes a gesture of a user wearing the input device and inputs information about the recognized gesture, and a method of inputting information using the same.

Related Art

With the advent of ubiquitous computing, computer environments have changed and various kinds of information input devices have been developed. Due to such technical changes, mobile keyboards have given way to input device which enable inputting information using a body part.

Korean Patent Registration No. 10-0634494 discloses a wearable information input device, an information processing device, and an information inputting method. This input device measures a distance between a specific portion of a finger and other portion of the finger in accordance with a bend of a finger, and selects an information input item.

Korean Patent Registration No. 10-1130150 discloses an input apparatus, an information process apparatus, and a control method of the input apparatus. The input device detects whether a pressing operation is being performed, by using a detected data value which is changed by a pressing operation or a touching operation of a surface of a sensor unit, detects a location where the pressing operation is being performed, and generate a control signal.

The present disclosure is made in association with a Korean national research and development project (research project name: Development of precise motion tracking and pressure sensing technology with flexible/ultra-thin/light weight strain and force sensors for finger motion tracking, project identification number: 10079763).

The disclosure of this section is to provide background of the invention. Applicant notes that this section may contain information available before this application. However, by providing this section, Applicant does not admit that any information contained in this section constitutes prior art.

SUMMARY

An embodiment of the present invention provides a device which recognizes movement of a body area by detecting a physical change in epidermis of the body area and inputs information based on the recognized movement.

An embodiment of the present invention provides an information input device which recognizes movement of a finger or a wrist by detecting a physical change in wrist epidermis caused by changes in wrist muscle.

An embodiment of the present invention provides an information inputting method for controlling an external device based on recognized movement of a body part.

An aspect of the present invention provides a wearable device including: a sensor array having a plurality of sensors each detecting a physical change in epidermis of a corresponding body area; and a body movement determination unit configured to determine movement of a body part based on sensing signals respectively received from the plurality of sensors.

A density of the plurality of sensors may be proportional to a density of muscles underneath of the epidermis of the corresponding body area.

The wearable device may further include a body movement pattern storage unit configured to store movement of the body part in conjunction with pre-defined sensing signal patterns of the plurality of sensors.

The body movement determination unit may detect a similarity level by comparing information about the received sensing signals with the pre-defined sensing signal patterns stored in the body movement pattern storage unit, and determine movement of the body part based on the similarity level.

The wearable device may further include a body movement transmission unit configured to transmit information about the determined movement of the body part to an external device over a communication network.

The sensor array may detect a strain on the epidermis of the corresponding body area.

The sensor array may be positioned in a wrist to detect a physical change in wrist epidermis, which is caused by changes in muscles including flexor pollicis longus and flexor digitorum profundus.

The wearable device may further include an inertial sensor positioned around an epidermis region of the corresponding body area, where a density of muscles is equal to or less than a specific level, and configured to measure an angular velocity and acceleration of movement of the body part.

The body movement determination unit may determine the movement of the body part based on the sensing signals respectively received from the plurality of sensors along with the angular velocity and the acceleration measured by the inertial sensor.

An aspect of the present invention provides a method of inputting information, including: detecting, by a sensor array having a plurality of sensors, a physical change in epidermis of a corresponding body area; and determining, by a body movement determination unit, movement of a body part based on sensing signals respectively received from the plurality of sensors.

The method may further include transmitting, by a body movement transmission unit, information about the determined movement of the body part.

The transmitting of information about the determined movement of the body part may include: identifying an Internet of Things (IoT) device that is linked over a communication network; and controlling the IoT device by transmitting the information about the determined movement of the body part to the IoT device.

The wearable device according to an embodiment of the present invention recognizes movement of a body part by recognizing a physical change in epidermis of a body area.

The wearable device according to an embodiment of the present invention recognizes movement of a finger or a wrist by detecting a physical change in wrist epidermis caused by changes in wrist change, and inputs information based on the recognized movement.

The wearable device according to an embodiment of the present invention controls an external device based on recognized movement of a body part.

DESCRIPTION OF EMBODIMENTS

Figure 1:
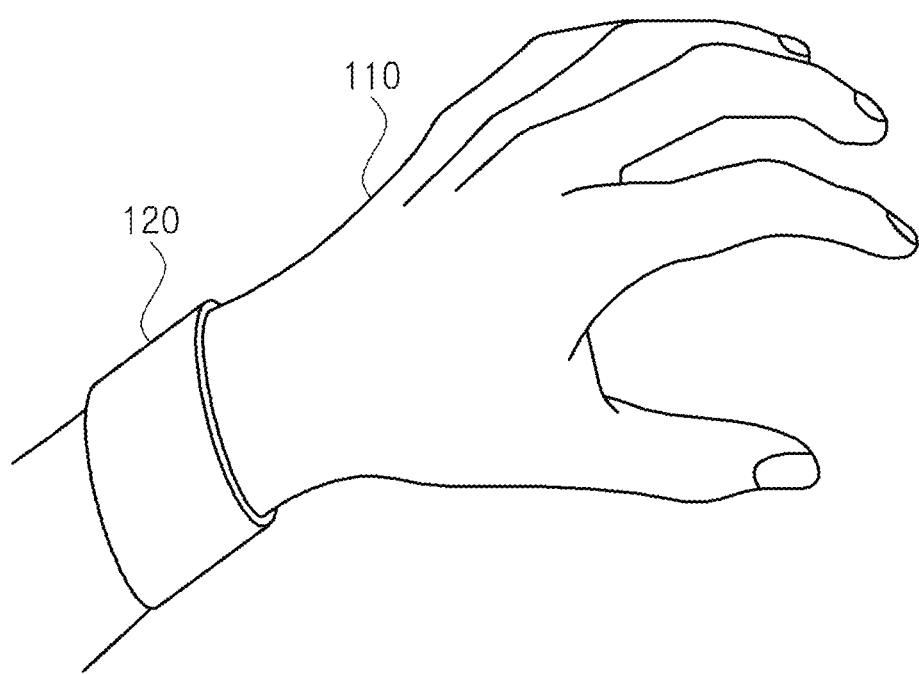
FIG. 1 is a diagram illustrating a wearable device according to an embodiment of the present invention.

Scope of the present invention is not limited to the embodiments explained in the disclosure. That is, since embodiments of the invention may be implemented in several forms without departing from the characteristics thereof, it should also be understood that the described embodiments are not limited by any of the details of the foregoing description, unless otherwise specified, but rather should be construed broadly within its scope as defined in the appended claims. Therefore, various changes and modifications that fall within the scope of the claims, or equivalents of such scope are therefore intended to be embraced by the appended claims.

Terms described in the present disclosure may be understood as follows.

While terms such as "first" and "second," etc., may be used to describe various components, such components must not be understood as being limited to the above terms. The above terms are used to distinguish one component from another. For example, a first component may be referred to as a second component without departing from the scope of rights of the present invention, and likewise a second component may be referred to as a first component.

It will be understood that when an element is referred to as being "connected to" another element, it can be directly connected to the other element or intervening elements may also be present. In contrast, when an element is referred to as being "directly connected to" another element, no intervening elements are present. In addition, unless explicitly described to the contrary, the word "comprise" and variations such as "comprises" or "comprising," will be understood to imply the inclusion of stated elements but not the exclusion of any other elements. Meanwhile, other expressions describing relationships between components such as "between", "immediately between" or "adjacent to" and "directly adjacent to" may be construed similarly.

Singular forms "a", "an" and "the" in the present disclosure are intended to include the plural forms as well, unless the context clearly indicates otherwise. It will be further understood that terms such as "including" or "having," etc., are intended to indicate the existence of the features, numbers, operations, activities, components, parts, or combinations thereof disclosed in the specification, and are not intended to preclude the possibility that one or more other features, numbers, operations, actions, components, parts, or combinations thereof may exist or may be added.

Identification letters (e.g., a, b, c, etc.) in respective steps are used for the sake of explanation and do not describe order of respective steps. The respective steps may be changed from a mentioned order unless specifically mentioned in context. Namely, respective steps may be performed in the same order as described, may be substantially simultaneously performed, or may be performed in reverse order.

Embodiments of the present invention may be implemented as computer-readable codes on computer-readable recording media. The computer readable recording media may be any data storage devices that can store data that can be thereafter read by a computer system. Examples of the computer-readable recording medium include ROM, RAM, CD-ROM, magnetic tapes, floppy disks, optical data storage, etc. Further, the computer-readable recording medium may be distributed over computer systems coupled via a network so that the computer-readable codes can be stored and executed in a distributed fashion.

Unless otherwise defined herein, all terms used herein including technical or scientific terms have the same meanings as those generally understood by a person skilled in the art. Terms defined in dictionaries generally used should be construed to have meanings matching with contextual meanings in the related art and are not to be construed as having an ideal or excessively formal meaning unless otherwise defined herein.

FIG. 1 is a diagram illustrating a wearable device according to an embodiment of the present invention.

Referring to FIG. 1, a user may wear a wearable device 120 on a body area 110 to input information. For example, the wearable device 120 of FIG. 1 may be worn on the user's wrist in the form of a band or a bracelet which uses a flexible sensor array, and the wearable device 120 receives information in response to the movement of the user's hand.

That is, wearing the wearable device 120 on a wrist, the user may input desired information by moving a hand on which the wearable device 120 is worn. The wearable device 120 may detect a physical change in epidemies of a corresponding body area in response to movement of the user's body part, determine movement of the body part, and receive information intended by the user.

FIG. 1 shows an example in which a user wears a wearable device on a wrist, but a certain embodiment of the present invention may be implemented as a wearable device which can be worn on or attached to a body part other than the wrist. In this case, the wearable device may take other forms to be easily worn on or attached to the corresponding part.

Figure 2:
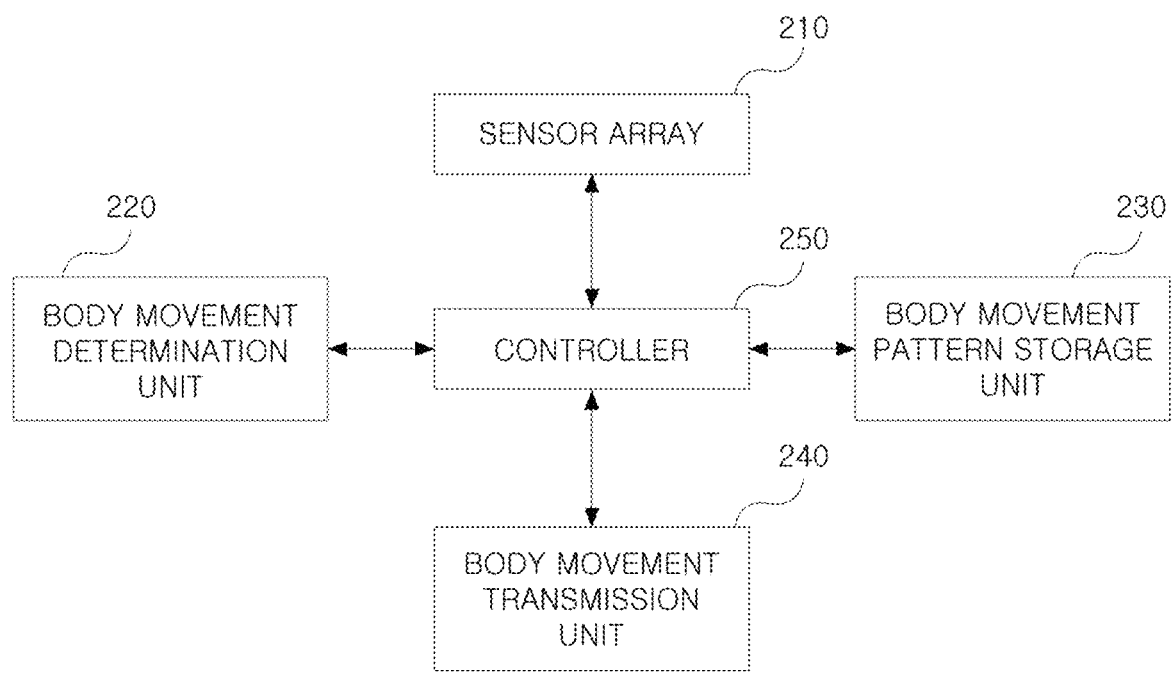
FIG. 2 is a block diagram illustrating a configuration of the wearable device shown in FIG. 1.

FIG. 2 is a block diagram illustrating a configuration of the wearable device shown in FIG. 1.

Referring to FIG. 2, the wearable device 120 may include a sensor array 210, a body movement determination unit 220, a body movement pattern storage unit 230, a body movement transmission unit 240, and a controller 250.

The sensor array 210 may detect a physical change in epidermis of a body area in contact with a plurality of sensors. The sensor array 210 may convert the physical change into an electric signal and output the signal, and may be positioned in a direction opposing the corresponding body area so as to easily detect the physical change in the epidermis. In one embodiment, the sensor array 210 includes a plurality of sensors arranged with a non-uniform density and detects epidermis strain. In one embodiment, a density of a plurality of sensors is proportional to a density of muscles underneath the epidermis of the corresponding body area. For example, a plurality of sensors may be positioned densely underneath the epidermis of a body area where muscles are dense, whereas a plurality of sensors may not be positioned densely underneath the epidermis of a body area where muscles are not dense.

In one embodiment, the sensor array 210 is implemented as a flexible tactile sensor array and detect epidermis strain.

The body movement pattern storage unit 230 stores movement of each body part in conjunction with pre-defined sensing signal patterns of a plurality of sensors in the sensor array 210. Sensing signal patterns and information about movement of body parts respectively corresponding to the sensing signal patterns may be defined by a developer and stored in the body movement pattern storage unit 230 in advance. If the corresponding information is defined more, the wearable device 120 may recognize more types of movement and receive more types of information based on the recognized movement.

The body movement determination unit 220 determines movement of a body part based on sensing signals respectively received from the plurality of sensors in the sensor array 210. In one embodiment, the body movement determination unit 220 compares a sensing signal detected by the sensing array 210 with sensing signal patterns stored in the body movement pattern storage unit 230 to search for if there is a sensing signal pattern matching the detected sensing signal. In one embodiment, the body movement determination unit 220 detects a similarity level by comparing sensing signals respectively received from the plurality of sensors with the sensing signal patterns. The similarity level may correspond to how the received sensing signals are similar with a specific sensing signal pattern, that is, whether the received sensing signals matches the specific sensing signal pattern within a preset error range.

In one embodiment, the body movement determination unit 220 searches for a pattern that matches the received sensing signals within the present error range. If a matching pattern is found, the body movement determination unit 220 may recognize movement of a body part corresponding to the matching pattern as a user's movement. If a matching pattern is not found, the body movement determination unit 220 ignores the sensing signals detected by the sensing array 210 and waits again.

The body movement transmission unit 240 transmits information about a body part's movement determined by the body movement determination unit 220 to an external device over a communication network. For example, the body movement transmission unit 240 may transmit information to an external device that is linked to the wearable device 120 over a communication network. In doing so, the wearable device 120 may control the external device or input information into the external device.

In one embodiment, the wearable device 120 includes a power unit. The power unit may supply power required for operation of the wearable device 120. For example, the power unit may be a battery, and may be a replaceable or chargeable type. In the case of the chargeable-type, the power unit may be charged using a wired charging means or a wireless charging means.

The controller 250 may control operation or data flow of the sensor array 210, the body movement determination unit 220, the body movement pattern storage unit 230, and the body movement transmission unit 240.

Figure 3A:
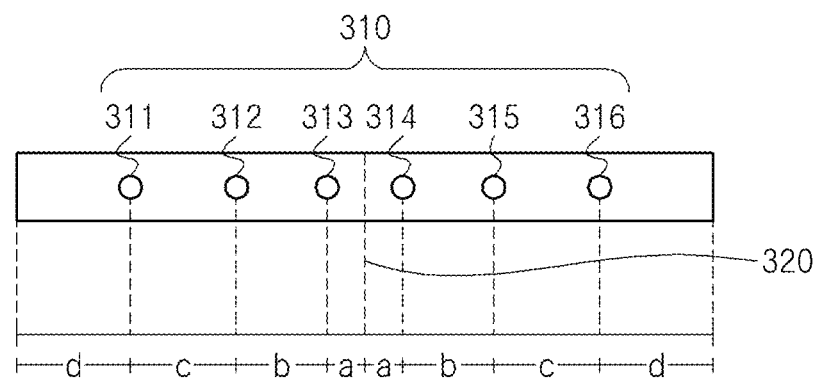
FIGS. 3A and 3B illustrate an example of the sensor array shown in FIG. 2.
Figure 3B:
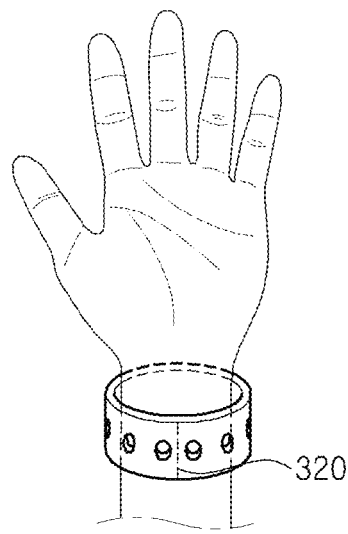

FIGS. 3A and 3B show a diagram illustrating an example of the sensor array shown in FIG. 2.

Referring to FIG. 3A, the sensor array 210 may include a plurality of sensors 310, and the plurality of sensors 310 may include a first sensor 311, a second sensor 312, a third sensor 313, a fourth sensor 314, a fifth sensor 315, and a sixth sensor 316, and detect a physical change in epidermis of a body area in contact.

In the case where the sensor array 210 is worn on a wrist and a central line 320 of the sensor array 210 is positioned in a lower part of the wrist, as shown in FIG. 3B, the plurality of sensors 310 may be arranged with distances of a, b, c, and d therebetween based on a density of muscles of the wrist. More specifically, more muscles are positioned densely in the lower wrist part than in the upper wrist part, and thus, the plurality of sensors 310 may be arranged with distances of a<b<c<d. That is, a density of sensors 310 positioned in the lower wrist part is greater than a density of sensors 310 positioned in the upper wrist part. Furthermore, the plurality of sensors 310 may be arranged to allow each of the plurality of sensors 310 to efficiently detect a physical change in epidermis of a body area in accordance with a type of a body part in contact or a location of muscles of the body part in contact.

Each of the plurality of sensors 310 in the sensor array 210 in FIG. 3A may detect epidermis strain of a body area in contact. For example, in the case of the wearable device 120 shown in FIG. 1, the sensor array 210 may detect a minute epidermis strain of a body area around the wrist, which is caused by changes in wrist muscles.

Figure 5C:
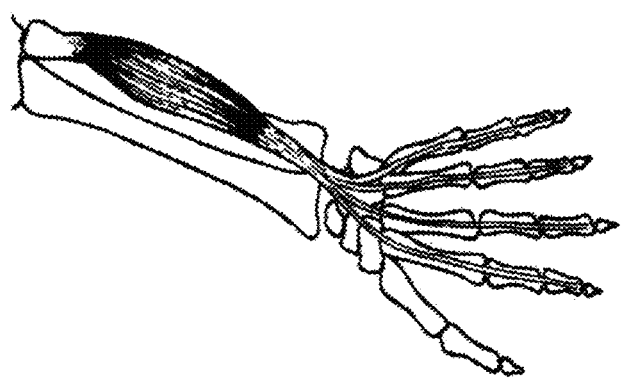
FIGS. 5A, 5B and 5C illustrate finger and wrist muscles.
Figure 5B:
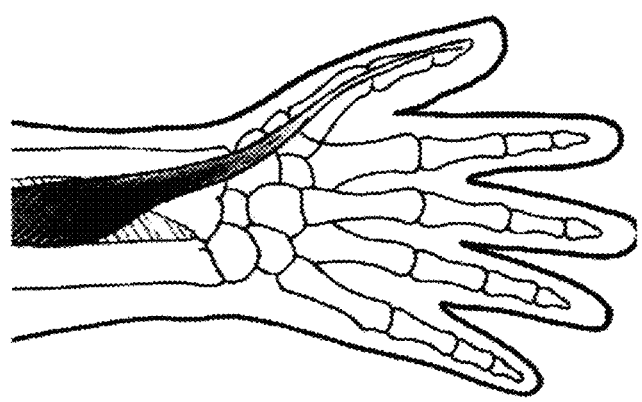
Figure 5A:
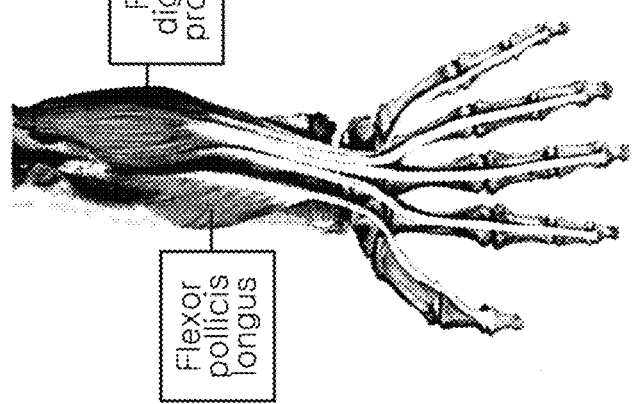

For example, take an example of finger and wrist muscle shown in FIG. 5A to FIG. 5C. A human moves his/her hand by moving the flexor pollicis longus and the flexor digitorum profundus which penetrate his/her wrist. That is, if the flexor pollicis longus and the flexor digitorum profundus moves, a hand and a wrist where the flexor pollicis longus and the flexor digitorum profundus are positioned moves accordingly. FIG. 5A shows finger and wrist muscles, FIG. 5B shows the flexor pollicis longus, and FIG. 5C shows the flexor digitorum profundus.

In the case where the sensor array 210 is positioned around a wrist, the sensor array 210 detects an epidermis strain caused by movement of the flexor pollicis longus and the flexor digitorum profundus, converts the movement into an electric signal. Then, the body movement determination unit 220 compares the electric signal received from the sensor array 210 with sensing signal patterns stored in the body movement pattern storage unit 230. If there is a sensing signal pattern matching the received electric signal, the body movement determination unit 220 may recognize movement corresponding to the matching pattern as a user's hand movement.

In one embodiment, the body movement pattern storage unit 230 stores pre-defined sensing signal patterns based on sensing signals respectively detected by the plurality of sensors 310. More specifically, the body movement pattern storage unit 230 may define a sensing signal pattern based on whether a first sensor 311, a second sensor 312, a third sensor 313, a fourth sensor 314, a fifth sensor 315, and a sixth sensor 316 detect a physical change in epidermis of a body area in contact, in addition to a degree of the epidermis strain in the case where the first sensor 311, the second sensor 312, the third sensor 313, the fourth sensor 314, the fifth sensor 315, and the sixth sensor 316 detect the physical change. For example, referring to [Table 1], sensing signal patterns corresponding to {(First Sensor, Yes), (Second Sensor, Yes), (Third Sensor, No), (Fourth Sensor, No), (Fifth Sensor, No), (Sixth Sensor, Yes)} may be stored in conjunction with movement of clenching a fist. If sensing signals received from the plurality of sensors 310 of the sensor array 210 correspond to {(First Sensor, Yes), (Second Sensor, Yes), (Third Sensor, No), (Fourth Sensor, No), (Fifth Sensor, No), (Sixth Sensor, Yes)}, a user who is wearing the wearable device 120 may be recognized as clenching a fist.

TABLE 1

| | First Sensor | Second Sensor | Third Sensor | Fourth Sensor | Fifth Sensor | Sixth Sensor | Movement |
|---|---|---|---|---|---|---|---|
| Whether physical change is detected | Yes | Yes | No | No | No | Yes | Clenching Fist |
| | Yes | No | Yes | Yes | No | Yes | Moving Wrist Upward or Downward |
| | No | No | Yes | Yes | No | No | Twisting Wrist |

Figure 4A:
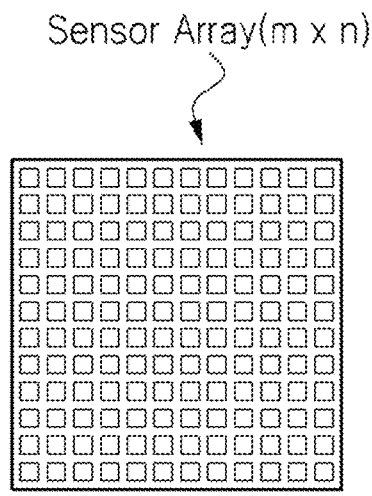
FIGS. 4A, 4B and 4C illustrate an example of a sensor included in the sensor array shown in FIG. 3.
Figure 4B:
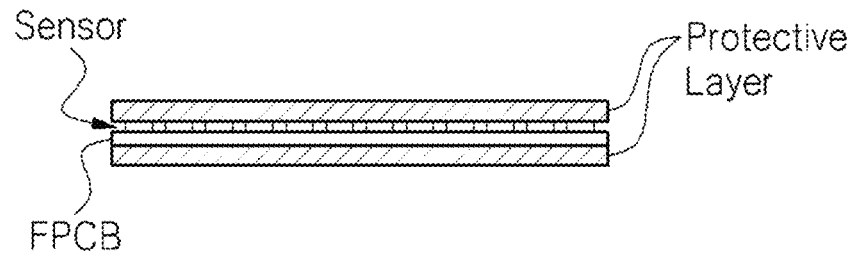

FIGS. 4A and 4B show an example of a sensor included in the sensor array shown in FIG. 3A and FIG. 3B.

Each of the plurality of sensors 310 included in the sensor array 210 may be implemented as in FIGS. 4A and 4B.

Referring to FIG. 4A and FIG. 4B, the plurality of sensors 310 may be an array composed of a plurality of tactile sensors and detect a physical change in a contact epidermis. A tactile sensor is a sensor that detects a physical properties of a contact region and converts the physical change into an electric sensor. A silicon-based CMOS tactile sensor, a polymer-based tactile sensor, a pressure sensitive material-based tactile sensor, and the like may be used as a tactile sensor. In one example, each of the plurality of sensors 310 includes a flexible printed circuit board (FPCB) substrate, on which a plurality of tactile sensors is mounted in an array, and polymer protective layers deposited above and below the FPCB on which the tactile sensors are mounted.

In one example, each of the plurality of sensors 310 is tactile sensors arranged in an m×n array, but other arrangement of sensors may be applied to the tactile sensor according to a type of a contact subject region as long as a physical change is detected efficiently.

Referring to FIG. 4B, each of the plurality of sensors 310 may include a flexible tactile sensor module. The flexible tactile sensor module may have a port connected to an electrode line of a tactile sensor. The port is a flat cable-type which can be manufactured together with a tactile sensor. In addition, it is possible to implement a flexible tactile sensor module having a signal processing connection part which is in the shape of a flexible flat cable (FFC).

In one embodiment, the flexible tactile sensor module includes a strain gage 420, an insulation film 411 and 412, a first electrode line 460, a second electrode line 430, a first opening 451, a second opening 452, and a supporter 450. The flexible tactile sensor module may include the strain gauge 420, the insulation films 411 and 412 surrounding the strain gauge 420, the first electrode line 460 connected to one end of the strain gauge 420 and formed on the inside and a surface of the insulation films 411 and 412, the second line 430 connected to the other end of the strain gauge 420 and formed in the inside and a surface of the insulation film 411 and 412, the first opening 451 enabling a part of the strain gauge 420 to rise, the second opening 452 exposing the second electrode line 450 and the supporter 450 formed below the insulation film 411 and 412.

In one embodiment, the insulation films 411 and 412 are separated into a first insulation layer 411 and a second insulation layer 412. One end of the strain gauge 420 may be connected and arranged between the first insulation layer 411 and the second insulation layer 412. The second electrode line 430 may be connected to the other end of the strain gage 420 in the second insulation layer 412 and arranged along the surface of the first insulation layer 411.

In embodiments, the second opening 452 further includes a plated layer that is plated on the first and second electrode lines 460 and 430.

In one embodiment, the insulation films 411 and 412 are composed of a flexible polymer.

Figure 4C:
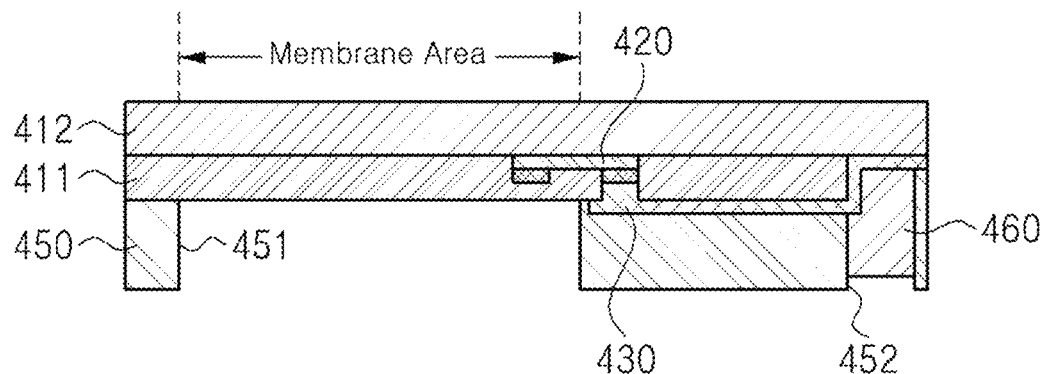

In one embodiment, the sensor array 210 including the plurality of sensors 310 implemented as in FIG. 4A to FIG. 4C detects epidermal strain of a contact region using the plurality of sensors 310 arranged in arrays. For example, the sensor array 210 is able to detect epidermal strain of the contact region using each of the plurality of sensors 310 which includes a plurality of tactile sensors arranged in arrays. For example, in the case of the wearable device 120 shown in FIG. 1, the sensor array 210 may detect a minute epidermal strain around a wrist, which is caused by changes in wrist muscles.

Figure 6:
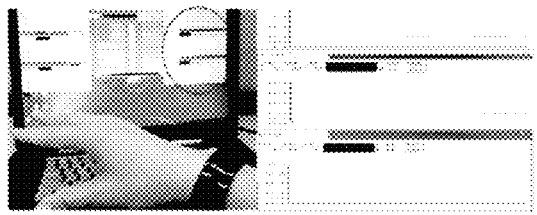
FIG. 6 is a diagram illustrating a process of detecting a physical change in the epidermis based on an angular velocity and acceleration using the wearable device shown in FIG. 1.
Figure 6:
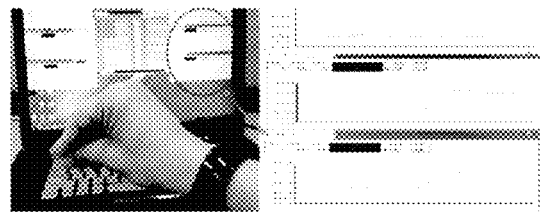
Figure 6:
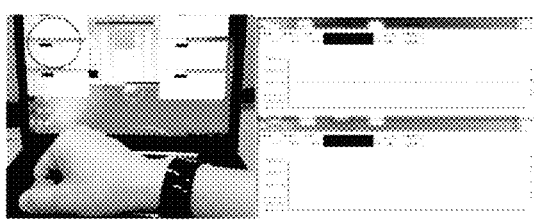
Figure 6:
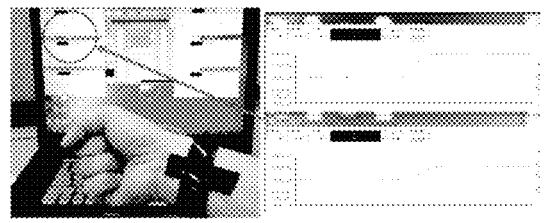
Figure 6:
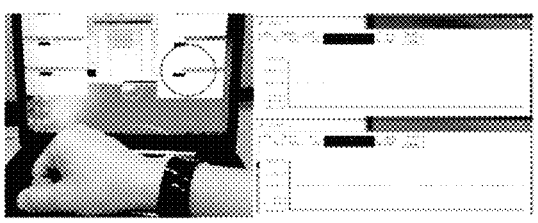
Figure 6:
Figure 6:
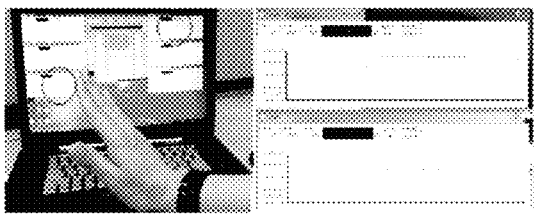
Figure 6:
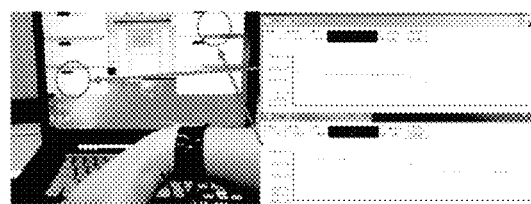

FIG. 6 is a diagram illustrating a process of detecting a physical change in the epidermis based on an angular velocity and acceleration using the wearable device shown in FIG. 1.

Referring to FIG. 6, using the wearable device 120, it is possible to detect strain in finger or wrist epidermis and output a signal in response to the detected strain. In FIG. 6, grabbing with fingers, twisting a wrist, stretching a finger, and moving a wrist upward and downward are illustrated as examples. However, the wearable device 120 can detect strain in wrist epidermis in response to various types of movement, and recognize movement of a hand (at least one of a finger and a wrist) based on the detected strain.

For example, referring to FIG. 6, before and after movement of a finger or a wrist, different sensing signals are received from a plurality of sensors 310 in a sensor array 210, which is worn on the wrist, depending on a type of the movement. Thus, the body movement determination unit 220 may compare the sensing signals received from the sensor array 210 with sensing signal patterns stored in the body movement pattern storage unit 230 so as to determine a user's hand movement.

Figure 7:
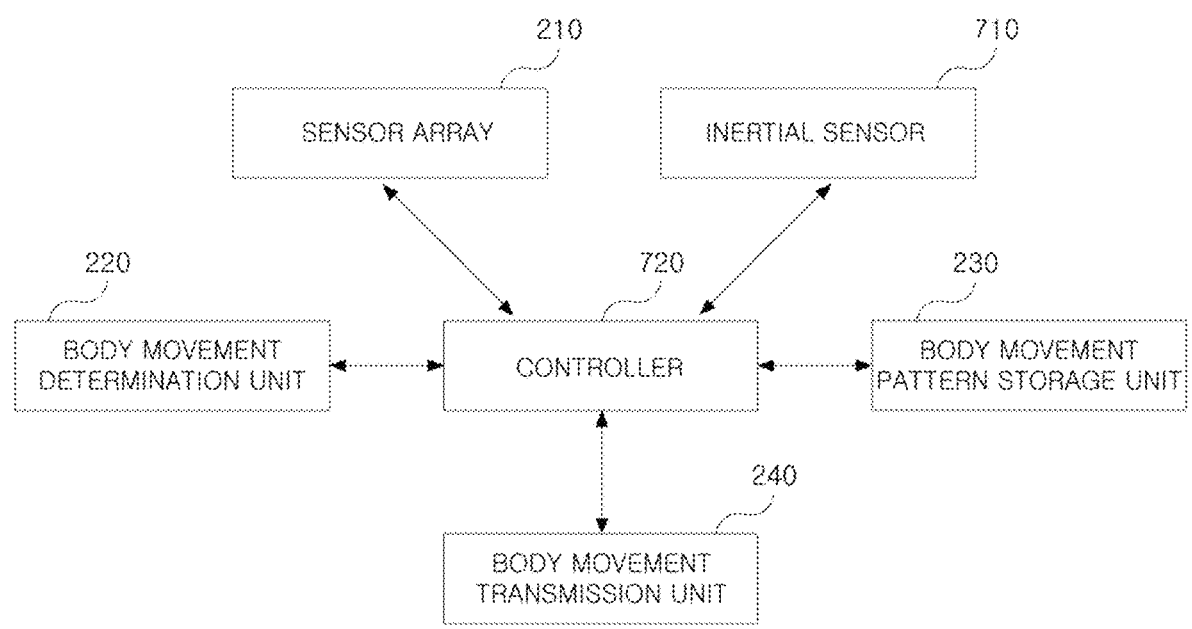
FIG. 7 is a diagram illustrating an example of a wearable device according to another embodiment of the present invention.

FIG. 7 is a diagram illustrating an example of a wearable device according to another embodiment of the present invention.

Referring to FIG. 7, the wearable device 120 includes an inertial sensor 710, a sensor array 210, a body movement determination unit 220, a body movement pattern storage unit 230, a body movement transmission unit 240, and a controller 720. In the following, only differences from the configuration shown in FIG. 2 will be described.

The inertial sensor 710 measures acceleration and an angular velocity of movement of a body part, and outputs an electric signal. The inertial sensor 710 may be included in the wearable device 120 or may be included in another device that a user is wearing or possessing.

In the example where the inertial sensor 710 is included in the wearable device 120, the inertial sensor 710 may be positioned around an epidermal region underneath a corresponding body area where a density of muscles is equal to or less than a specific level.

The sensor array 210 detects a physical change in epidermis of a body part in contact, converts the physical change into an electric signal, and outputs the electric signal.

The body movement pattern storage unit 230 may store a pre-defined physical change, an inertial pattern, and information about body movement corresponding to the corresponding inertial pattern.

The body movement determination unit 220 compares an electric signal (information about acceleration and angular velocity), which is output from the inertial sensor 710), and a signal indicative of a physical change in the epidermis, which is output from the sensor array 210, with the pre-defined physical change and the inertial pattern stored in the body movement pattern storage unit 230 so as to search for a matching pattern. The body movement determination unit 220 searches for a matching pattern within a preset error range. If a matching pattern is found, the body movement determination unit 220 recognizes body movement corresponding to the matching pattern as a user's movement.

For example, if a user wears the wearable device 120 and grabs an object, the body movement determination unit 220 may recognize the grabbing movement based on sensing signals indicative of a physical change in the epidermis of a corresponding body area, the signals which are received from the sensor array 210. Then, the body movement determination unit 220 may recognize pulling movement and a pulling direction based on an electric signal output from the inertial sensor 710.

The wearable device 120 transmits information about the recognition result to an external device through the body movement transmission unit 240 so as to control the external device or input information. For example, if the wearable device 120 is linked to a robot arm (an external device) and recognizes grabbing and pulling movement, the wearable device 120 may transmit the recognized information to the robot arm so as to control the robot arm so that the robot arm actually grabs and pulls an object. In another example, if the wearable device 120 is linked to a computer and recognizes grabbing and pulling movement, the wearable device 120 may transmit the recognized information to the computer so as to input a command of moving a screen or removing specific information.

The controller 720 controls operation and data flow of the inertial sensor 710, the sensor array 210, the body movement determination unit 220, the body movement pattern storage unit 230, and the body movement transmission unit 240.

Figure 8:
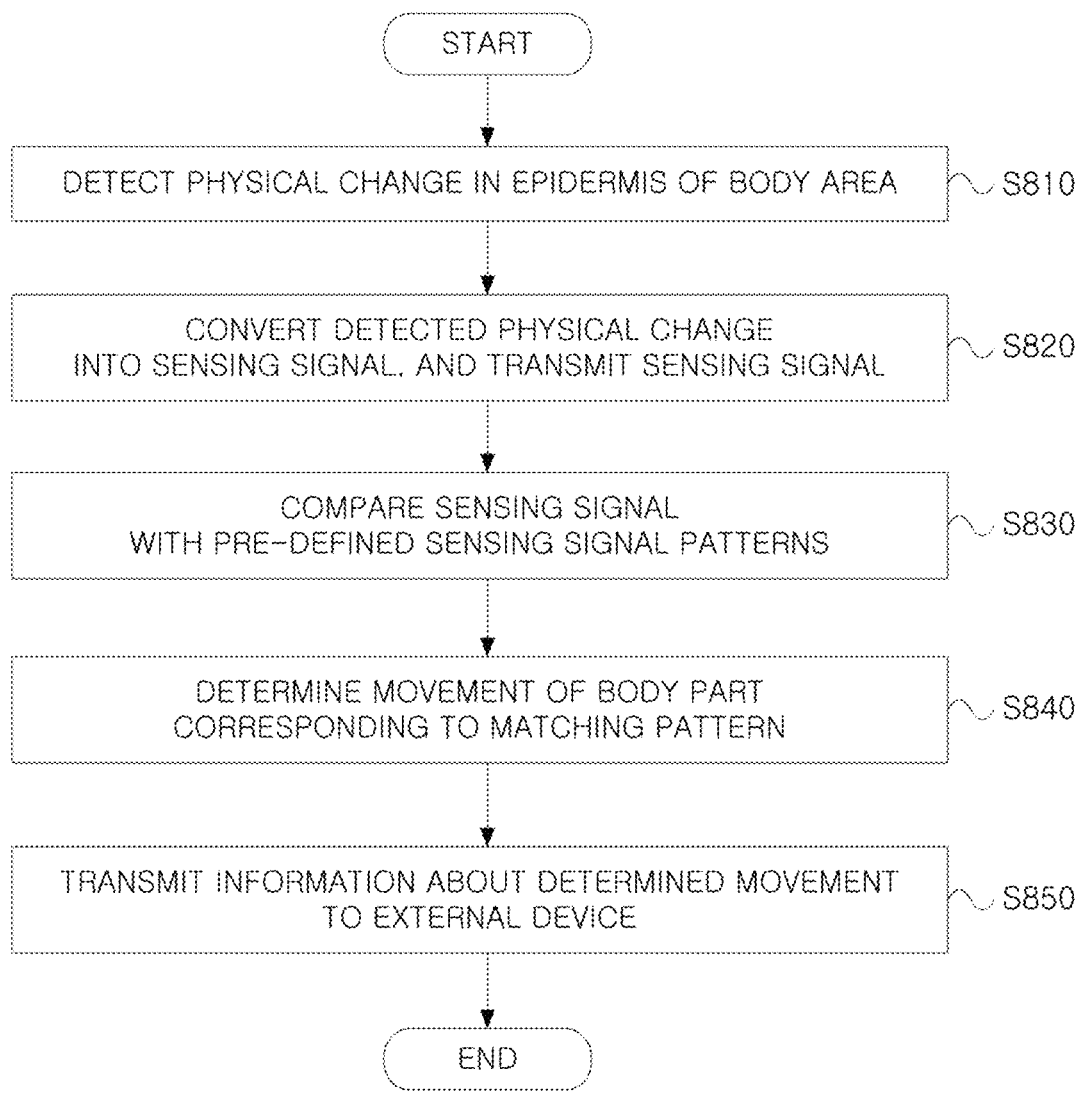
FIG. 8 is a flowchart illustrating a method of inputting information using a wearable device according to an embodiment of the present invention.

FIG. 8 is a flowchart illustrating a method of inputting information using a wearable device according to an embodiment of the present invention.

Referring to FIG. 8, the sensor array 210 detects a physical change in epidermis of a body area in contact in S810. For example, the sensor array 210 includes a plurality of sensors 10 or a tactile sensor array, and detect epidermal strain of a body area in contact. In the case of a wearable device worn on a wrist, the sensor array 210 may detect a physical change in epidermis of the wrist, which is caused by changes in wrist muscles.

The sensor array 210 converts the physical change, detected by the plurality of sensors 310, into a sensing signal and transmits the sensing signal to the body movement determination unit 220 in S820.

The body movement determination unit 220 may compare the sensing signal, received from the sensor array 210, with pre-defined sensing signal patterns stored in the body movement pattern storage unit 230 to see if there is any pre-defined sensing signal pattern matching the received sensing signal in S830. If there is a sensing signal pattern matching the received sensing signal, the body movement determination unit 220 may recognize body movement corresponding to the matching pattern as a user's movement in S840.

In one embodiment, the method of inputting information further includes measuring an angular velocity and acceleration of movement of a body area using the inertial sensor 710. In this case, the body movement determination unit 220 may recognize the user's movement based on information about a physical change in epidermis measured using the sensor array 210 along with the angular velocity and acceleration measured using the inertial sensor 710.

The body movement transmission unit 240 may transmit the information about movement of a body area, which is recognized by the body movement determination unit 220, to an external device over a wired or wireless communication network in S850. For example, the body movement transmission unit 240 may transmit information about movement to the external device over a short-ranged communication network, such as Bluetooth and Ultra Wide Band (UWB).

In one embodiment, when a user controls an Internet of Things (IoT) device using a wearable device, the body movement transmission unit 240 identifies the IoT device, which is linked to a wearable information input device over the wireless communication network, and transmits information about movement to the linked IoT device.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

Although embodiments of the present invention have been described for illustrative purposes, those skilled in the art will appreciate that various modifications, additions and substitutions are possible, without departing from the scope and spirit of the invention as disclosed in the accompanying claims.

Certain embodiments of the present invention relate to a wearable device, which recognizes a gesture of a user wearing the wearable device and inputs information based on the recognized gesture, and a method of inputting information using the same.

What is claimed is:

1. A wearable device comprising: a strap configured to surround a wrist;
   a sensor array comprising a plurality of sensors that are disposed along a longitudinal direction of the strap, each of the plurality of sensors configured to contact epidermis of the wrist and to detect a physical change in the epidermis;
   a body movement determination unit configured to determine movement of the wrist based on signals received from the plurality of sensors; and
   a body movement pattern storage unit configured to store movement of the wrist in conjunction with pre-defined sensing signal patterns of the plurality of sensors, wherein the plurality of sensors are spaced apart among each other based on a density of muscles underneath of the epidermis of the wrist when the wearable device is worn on the wrist such that the plurality of sensors are more densely arranged in a lower part of the wrist than an upper part of the wrist when the wearable device is worn on the wrist, wherein the plurality of sensors comprise a first sensor, a second sensor located next to the first sensor and a third sensor located next to the second sensor, wherein the first, second and third sensors are arranged in order along the longitudinal direction of the strap wherein the second sensor is located closer to the upper part of the wrist than the first sensor and the third sensor is located closer to the upper part of the wrist than the second sensor when the wearable device is worn on the wrist, and wherein the second sensor is apart from the first sensor by a first distance and the third sensor is apart from the second sensor by a second distance which is greater than the first distance.

2. The wearable device of claim 1, wherein the body movement determination unit is configured to detect a similarity level by comparing information about the received sensing signals with the pre-defined sensing signal patterns stored in the body movement pattern storage unit, and to determine movement of the wrist based on the similarity level.

3. The wearable device of claim 1, further comprising: a body movement transmission unit configured to transmit information about the determined movement of the wrist to an external device over a communication network.

4. The wearable device of claim 1, wherein the sensor array is configured to detect a strain on the epidermis of the wrist.

5. The wearable device of claim 1, further comprising: an inertial sensor configured to measure an angular velocity and acceleration of movement of the wrist.

6. The wearable device of claim 5, wherein the body movement determination unit is configured to determine the movement of the wrist based on the signals received from the plurality of sensors along with the angular velocity and the acceleration measured by the inertial sensor.

7. A method of operating a wearable device, the method comprising:

detecting, by a sensor array comprising a plurality of sensors, a physical change in epidermis of a wrist;

determining, by a body movement determination unit, movement of the wrist based on signals received from the plurality of sensors; and transmitting, by a body movement transmission unit, information about the determined movement of the wrist, wherein the plurality of sensors are spaced apart among each other based on a density of muscles underneath of the epidermis of the wrist when the wearable device is worn on the wrist such that the plurality of sensors are more densely arranged in a lower part of the wrist than an upper part of the wrist when the wearable device is worn on the wrist, wherein the plurality of sensors comprise a first sensor, a second sensor located next to the first sensor and a third sensor located next to the second sensor, wherein the first, second and third sensors are arranged in order along a longitudinal direction of the strap, wherein the second sensor is located closer to the upper part of the wrist than the first sensor and the third sensor is located closer to the upper part of the wrist than the second sensor when the wearable device is worn on the wrist, wherein the second sensor is apart from the first sensor by a first distance and the third sensor is apart from the second sensor by a second distance which is greater than the first distance.

8. The method of claim 7, wherein the transmitting comprises:

identifying an Internet of Things (IoT) device that is linked over a communication network; and controlling the IoT device by transmitting the information about the determined movement of the wrist to the IoT device.

* * * * *